Figure 1:
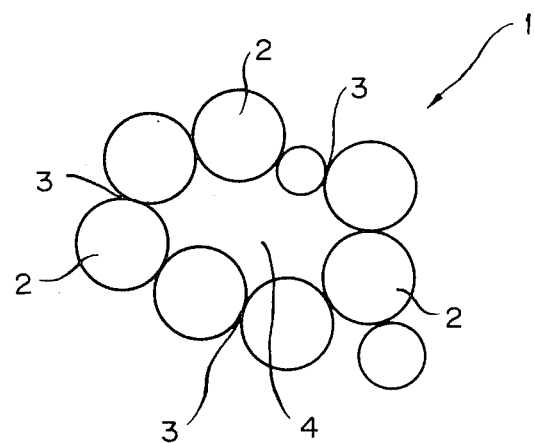

United States Patent [19]

Koyama et al.

[11] 4,430,436
[45] Feb. 7, 1984

[54] ANALYTICAL ELEMENT AND METHOD OF USE

[75] Inventors: Mikio Koyama; Shozo Kikugawa; Kenichiro Okaniwa; Kiyoshi Tamaki, all of Hino, Japan

[73] Assignee: Konishiroku Photo Industry Co., Ltd., Tokyo, Japan

[21] Appl. No.: 329,034

[22] Filed: Dec. 9, 1981

[30] Foreign Application Priority Data

Dec. 17, 1980 [JP] Japan ................. 55-179614

[51] Int. Cl.³ ............... G01N 21/78; G01N 33/52; G01N 33/54
[52] U.S. Cl. ................... 436/531; 422/56; 422/57; 428/327; 428/407; 428/420; 436/810; 523/206; 525/902
[58] Field of Search ............. 428/407, 420, 327; 525/902, 191, 208, 221, 223; 523/206; 210/506, 510; 422/56, 57, 58; 436/170, 531, 810

[56] References Cited

U.S. PATENT DOCUMENTS 2,297,248  9/1942  Rudolph .................. 210/496 X
4,258,001  3/1981  Pierce et al. ................ 422/56

*Primary Examiner*—Arnold Turk
*Attorney, Agent, or Firm*—Frishauf, Holtz, Goodman & Woodward

[57] ABSTRACT

An analytical element for analysis of a liquid having an interconnected void structure zone positioned on one side of a liquid-impermeable, light-transmissive support, being characterized in that said interconnected void structure zone comprises a bound particulate structure which is a three-dimensional lattice, being non-swellable in the liquid and having interconnected voids with a void volume of 25 to 85% among the particles to provide transport of said liquid, the material for said bound particulate structure being non-swellable in and impermeable to said liquid and said bound particulate structure being constituted of heat-stable, organic polymer particle units having reactive groups with particle sizes of 1 to 350 microns which are chemically bonded directly to each other through said reactive groups in the areas of contact. A method of analysis utilizing the analytical element in immunoassay is also disclosed.

29 Claims, 1 Drawing Figure

ANALYTICAL ELEMENT AND METHOD OF USE

This invention relates generally to analytical chemistry, particularly to an analytical element for analysis of a predetermined specific component in a liquid. More particularly, it pertains to a quantitative analytical element for assay of a specific component in a biological liquid sample.

These have been developed a great number of methods for analysis of components in liquid samples. For example, there may be mentioned automatic quantitative analytical devices. These are frequently used and very useful especially in clinical test laboratories in hospitals and the like. Such automatic analytical devices employ techniques based on continuous conveyor system analysis, in which samples, diluents and analytical reagents are mixed together and conveyed to analytical devices, as disclosed in, for example, U.S. Pat. No. 2,797,149.

Such continuous automatic analytical devices, however, are complicated and expensive, requiring skilled operators. In addition, repeated washing operations are required to be performed after the analytical operation and consume a great amount of time as well as labor, and the wastewaters resulting from these operations will disadvantageously involve the problem of causing environmental pollution.

On the other hand, as contrasted to the analytical system employing solutions as mentioned above, there is another analytical system employing dry chemistry. These are called as test papers or test strips provided in the dry form which are, prepared by dipping an absorptive carrier such as a filter paper in an analytical reagent solution followed by drying, as disclosed in, for example, U.S. Pat. No. 3,050,373 or U.S. Pat. No. 3,061,523. These test strips enable measurement by dipping in a liquid sample of analyte and then withdrawing to read the color change or density change on the test strip with the naked eye or by means of an instrument such as densitometer.

These test strips are easy handled and useful in giving instantly the test results. But, these test strips comprising reagents carried in absorptive carriers suffer from various vital defects, and therefore their applications are still limited to qualitative or semi-quantitative analysis.

For overcoming these defects, there has been developed an analytical element as disclosed in U.S. Pat. No. 3,992,158. These elements have a reagent layer containing analytical reagents and a spreading layer comprising an isotropically porous, non-fibrous medium laminated on a transparent support.

The spreading layers of said Patent are said to have three functions:

(1) to distribute a liquid sample uniformly in a constant volume per unit area throughout the reagent layer;

(2) to remove substances or factors which interfere with the analytical reaction in the liquid sample; and (3) to perform background action to reflect the light to be measured transmitted through the support in carrying out spectrophotometric analysis.

In said Patent, there is disclosed a porous film formed of diatomaceous earth particles, white pigments or inert white glass beads with the use of a polymer material binder such as cellulose esters.

Such a film is stated to have the three functions required for the spreading layer as mentioned above. These films, however, have only brittle strength, tending to break easily, and a stable supply of these films is difficult. Further, when a liquid sample containing cells such as blood cells or large conjugated proteins is applied to such a film, undesirable phenomena such as clogging of voids or ununiform permeation may disadvantageously occur. Also, from aspects of preparation, it is required to control severely the conditions for coating, and constant void volume (porosity) can hardly be obtained if such conditions are not satisfied. Further, microcrystalline colloidal particles, namely particulate substances such as microcrystalline cellulose tend to be swelled in the presence of an aqueous liquid sample. Accordingly, a porous particulate structure prepared from the above material has the disadvantage of partially or completely blocking the voids in the layer by application of a liquid sample thereby to impede markedly the fluid flow. As another embodiment in said Patent, there is also mentioned a porous layer structure formed of non-tacky particles such as inert glass beads or resins with the use of a hydrophilic colloid binder such as gelatin or polyvinyl alcohol.

However, in such a structure, the void volume in the porous layer will be changed depending on the quantity of the above binder. When the hydrophilic colloid is added to the extent so as to give sufficient adhesive strength, the void volume is decreased to impede the flow of a liquid sample. On the contrary, when the quantity of the binder is decreased, said layer structure is very brittle and cannot maintain its integrity. Further, the hydrophilic colloid, which is the adhesive soluble in water, will disadvantageously be further lowered in adhesive strength when an aqueous liquid sample is present. The porous layer disclosed in said Patent also involves the drawback of tending to be clogged with a number of macromolecular complex substances and cells in the voids to impede the fluid flow.

U.S. Pat. Nos. 2,297,247 and 2,745,141 discloses agglomerated particle layers in which the particles are heat- or solvent-softened and solidified. In such layers, the particles are fused with each other at the interparticle contact points. This means that the agglomerated particle layer has the disadvantage of being readily deformed through heat- or solvent-softening of the constituent particles to decrease or eliminate completely the desirable interparticle open spaces of the structure. U.S. Pat. No. 2,297,248 discloses a filter element which is a particulate structure prepared by adhereing together the particles with a "suitable cement". However, this structure also involves the drawback that the adhesive will readily fill the interparticle spaces depending on its quantity, whereby high molecular weight complex substances or cells readily clog and impede fluid flow in such a structure. Moreover, even a fluid flow containing no such substance at all may sometimes disadvantageously be retarded. In addition, there is also disclosed in Japanese Provisional Patent Publication No. 90859/1980 a porous particulate structure in which heat-stable, organic polymer particles non-swellable in and impermeable to the liquid are bonded with an adhesive of an organic polymer different from that of the particles into a coherent, three-dimensional lattice.

In said Patent, similarly as in the Patents previously mentioned, a particulate structure is formed having interconnected voids by effecting bonding between the heat-stable organic polymer particles with an adhesive polymer with low heat stability, namely having a low glass transition temperature ($T_g$), which is heat-softened at a temperature higher than $T_g$. Accordingly, when a large quantity of the adhesive is employed for formation of the particulate structure disclosed in said Patent, the void volume is decreased, while sufficient adhesive strength cannot be obtained with too little an amount of adhesive. Hence, it is difficult to control the void volume at a desired value, by using the above adhesive in an amount as defined and arranging all of the adhesive at desired positions between the above heat-stable polymer particles. Further, the particulate structure, formed through bonding between the inert beads only by deformation of heat-softened adhesive, has the disadvantage of low bonding strength.

The present inventors have made extensive studies and were successful in overcoming the drawbacks as mentioned above by use of an analytical element having the following constitution.

That is, the analytical element according to the present invention is an analytical element for analysis of a liquid having an interconnected void structure zone positioned on one side of a liquid-impermeable, light-transmissive support, being characterized in that said interconnected void structure zone comprises a bound particulate structure which is a three-dimensional lattice, being non-swellable in the liquid and having interconnected voids with a void volume of 25 to 85% among the particles to provide transport of said liquid, the material for said bound particulate structure being non-swellable to said liquid and said bound particulate structure being constituted of heat-stable, organic polymer particle units having reactive groups with particle sizes of 1 to 350 microns which are chemically bonded directly to each other through said reactive groups in the areas of contact.

The interconnected void structure comprising the bound particulate structure according to the present invention can readily take up or effect separative filtration of a liquid sample, especially many high molecular weight substances and cells such as red blood cells dissolved or dispersed in biological liquid samples or interactive compositions used in liquid analysis procedures without clogging or otherwise substantially impeding fluid transport.

FIG. 1 which is attached hereto shows a partial structure of the bound particulate structure zone consisting of heat-stable polymer particle units containing reactive groups according to the present invention.

In FIG. 1, reference numerals 1 to 4 denote the partial structure of the bound particulate structure zone, heat-stable polymer particle units, chemically bonded sites with reactive groups and interconnected voids, respectively.

The analytical elements of the present invention can perform a highly efficient spreading function for liquids containing either low or high molecular weight substances of analytical interest (hereinafter termed analytes). That is, these elements have a particulate structure which can readily take up, uniformly distribute within itself, meter and rapidly transport applied liquid samples containing any of a wide variety of analytes.

The interconnected void structure of bound particulate structure formed of heat-stable polymer particle units having reactive groups according to the present invention is produced through mutual reaction between the reactive groups of the particle units in the areas of contact to form a three-dimensional lattice, and the particle units are bonded to each other firmly through chemical bonding. Thus, it is evident that said structure has a strength sufficient to maintain its appearance and structure against external physical force.

The above polymer particle units have sizes preferably of about 1 to 350 microns, and these particles form a bound particulate structure which is a three-dimensional lattice including interconnected voids, of which the total void volume is about 25 to 85%.

The material for the bound particulate structure impermeable to and non-swellable in a liquid of the invention means that it is substantially impermeable to said liquid and substantially free from swellability when contacted with the liquid. The degree of swellability can be determined in the presence of the desired liquid by use of a swellometer of the type described in A. Green and G. I. P. Levenson, Journal of Photographic Science, 20, 205 (1972). That is, the test can be carried out by forming (1) a self-supporting film of the specific polymer under consideration for use as a particle material, or (2) a layer of the polymer, such layer having a dry thickness in the range of from 50 to 200 microns, on a suitable support, for example, a poly(ethyleneterephthalate) support, and determining the percent increase in the film or layer thickness which results from immersing the dry film or layer into a liquid bath at 38° C. for about 2.5 minutes. There may preferably be employed a polymer particle material having a swellability less than about 20%, preferably less than about 10%, as measured by these methods.

The size of the polymer particle units constituting the bound particulate structure of the present invention can vary widely within the range as specified above, and it is possible to use a mixture of particles with various sizes. But, in a preferred embodiment, these particles are of substantially uniform size. Preferably, the particles have a curvilinear surface and, more preferably, are substantially spherical. The size of the organic polymer particle units regulates, to some extent, the size of the voids contained in the interconnected void structure layer. In a preferred embodiment, wherein the element is intended for the transport of liquid samples containing complete cellular structures, such as red blood cells, which can attain a size range of from about 6 to 8 microns, one would select relatively large size particle units. In such case, particle sizes within the range of from 20 to 300 microns, preferably 20 to 150 microns, can be employed.

In the case where one is concerned with the transport of large, complex molecules, such as macromolecules of biological origin, for example, lipoproteins and antigens, particles having a size range on the order of from 1 to 100 microns, preferably 2 to 50 microns, more preferably 2 to 20 microns, can be employed. In the case of aqueous fluids containing analytes of still smaller molecular size, for example, glucose molecules and uric acid molecules, one can employ particles having a size range of from 1 to 30 microns.

The chemical bondings between the adjacent particle units may be formed either by the mutual reaction between the adjacent particle units having the same kind of reactive groups, for example, between the particle units having epoxy groups, or by the reaction between the particle units having different kinds of reactive groups, for example, between the particle unit having an epoxy group and the particle unit having an amino group. Each particle unit may also have two or more kinds of reactive groups. If desired, heating or a catalyst may be employed for effecting chemical bonding between the reactive groups. The particle units having reactive groups can be prepared, for example, by homopolymerization or copolymerization of monomers having reactive groups or precursors thereof. The particle units having two or more kinds of reactive groups can be prepared, for example, by copolymerization of monomers having different kinds of reactive groups or precursors thereof. When monomers having precursors of the reactive groups are employed, they can be converted to particle units having the reactive groups, for example, after formation of the particle units, by the treatment such as hydrolysis. In the present invention, the monomer units having reactive groups may be contained in an amount of preferably about 0.1 to about 30% by weight based on the polymer particle units, particularly 0.5 to 20%.

As the monomers suitable for formation of chemical bonding by the reaction between the adjacent particle units having the same kind of reactive groups, there may be mentioned monomers having epoxy groups, monomers having aziridyl groups, monomers having formyl groups, monomers having hydroxymethyl groups, monomers having isocyanate groups, monomers having thiol groups and monomers having carbamoyl groups.

As a monomer having an epoxy group, there may be mentioned, for example, glycidyl acrylate, glycidyl methacrylate, allyl glycidyl ether, 4-vinylcyclohexane monoepoxide, etc. A monomer having an aziridyl group may be exemplified by aziridylethyl methacrylate, 1-ethylenesulfonyl aziridine, 1-ethylenecarbonyl aziridine, aziridylethyl acrylate, etc. Typical examples of a monomer having a formyl group are acrolein and methacrolein. A monomer having a hydroxymethyl group may include, for example, N-methylol-acrylamide, N-methylol-methacrylamide, N-methyloldiacetoneacrylamide, and the like. Typical examples of a monomer having an isocyanate group are vinyl isocyanate and allyl isocyanate. Examples of a monomer having a thiol group are vinyl thiol, p-thiol styrene, m-thiol styrene, vinyl benzyl thiol and acetyl derivatives of these. As a monomer having a carbamoyl group, there may be included, for example, acrylamide, methacrylamide, maleinamide, diacetone acrylamide, etc.

As other monomers to be copolymerized with the monomers having reactive groups, there may be selected any monomer, so long as the resultant bound particulate structure satisfies the conditions of liquid impermeability and non-swellability.

As combinations of different kinds of reactive groups to be used in the case of formation of chemical bonding through the reaction between the particle units having different kinds of reactive groups, there may be mentioned those as set forth in D. H. Solomon "The Chemistry of Organic Film Formers" (1967). More specifically, there may be mentioned epoxy and amino, carboxyl and amino, carbamoyl and hydroxymethyl, carbamoyl and methoxy, hydroxymethyl and carboxymethoxymethyl, hydroxyl and carboxyl, epoxy and —COOC$_4$H$_9$(t), ureido and carboxyl, formyl and hydroxyl, vinylsulfonyl and amino, haloethylsulfonyl and amino, active methylene containing group and formyl, epoxy and carboxyl, aziridyl and amino, aziridyl and carboxyl, and so on.

Among the monomers having various reactive groups as mentioned above, typical examples of the monomers having epoxy group, aziridyl group, hydroxyl group or carbamoyl group may be inclusive of those mentioned hereinabove. Examples of monomers having other reactive groups are as follows. As a monomer having carboxyl group, there may be mentioned acrylic acid, methacrylic acid, itaconic acid, maleic acid, itaconic acid half-ester, maleic acid half-ester, etc. A monomer having an amino group may be exemplified by aminostyrene, N,N-dimethylaminoethyl acrylate, N,N-dimethylaminoethyl methacrylate. Typical examples of a monomer having a methoxy group are methoxyethyl acrylate, ethoxyethyl acrylate, methoxyethyl methacrylate, ethoxyethyl methacrylate, and the like. As a monomer having —COOC$_4$H$_9$(t) group, there may be included tert-butyl acrylate, tert-butyl methacrylate. Examples of a monomer having a ureido group are ureidoethyl acrylate, ureidoethyl methacrylate, ureidovinyl ether (e.g., those represented by the formula CH$_2$=CHONRCONHR', wherein R represents a hydrogen atom or a methyl and R' a hydrogen atom or a lower alkyl such as methyl or ethyl). As a monomer having a hydroxyl group, there may be mentioned 2-hydroxyethyl acrylate, 2-hydroxyethyl methacrylate, 2-hydroxypropyl methacrylate, 2-hydroxypropyl acrylate, etc. A monomer having a haloethylsulfonyl group may be exemplified by chloroethylsulfonylethyl methacrylate, bromoethylsulfonylethyl methacrylate, etc. A typical example of a monomer having a vinylsulfonyl group is vinylsulfonylethyl methacrylate. Examples of a monomer having an active methylene containing group are acryloyl acetone and methacryloyl acetone. As a monomer having a carboxymethoxymethyl group, there may be mentioned, for example, N-carboxymethoxymethyl-acrylamide and N-carboxymethoxymethyl-methacrylamide.

When there are employed particle units having two or more kinds of reactive groups as mentioned above, chemical bonds between the same kinds of the reactive groups as mentioned above as well as the chemical bonds between the different kinds of reactive groups will be formed. It is also possible to form a bound particulate structure by use of two kinds or more of particle units having reactive groups.

Examples of other preferable monomers to be copolymerized with the monomers having reactive groups as described above are set forth below.

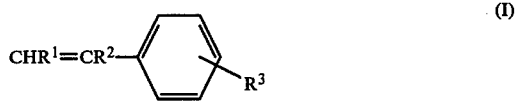

(I)

wherein each of R$^1$ and R$^2$, which can be the same or different, represents a non-interfering substituent such as a hydrogen atom, a halogen atom, or a substituted or unsubstituted, amino-free alkyl or aryl group having 1 to 10 carbon atoms and R$^3$ represents a hydrogen atom, a halogen atom, or a substituted or unsubstituted, amino-free aliphatic or aromatic group having 1 to 10 carbon atoms.

As aliphatic or aromatic groups, there may be included alkyl groups, alkoxy groups, aryl groups and aryloxy groups. Typical examples of the monomers represented by the formula (I) are styrene, vinyltoluene, vinylbenzyl chloride, t-butylstyrene, etc.

$$CHR^6=CR^4—COOR^5 \qquad (II)$$

wherein $R^6$ has the same meaning as $R^1$ in the formula (I), $R^4$ represents a hydrogen atom or a methyl and $R^5$ represents an aryl, an alkyl an alkaryl and aralkyl group, each having 1 to 10 carbon atoms.

(III) Polymerizable unsaturated nitrile monomers such as acrylonitrile and methacrylonitrile.

(IV) Interparticle crosslinking monomers having two addition-polymerizable groups such as divinylbenzene, N,N-methylene-bis(acrylamide, ethylene diacrylate and ethylene dimethacrylate).

By copolymerization of a suitable combination of these monomers with the aforesaid monomers having reactive groups, it is possible to constitute the polymer particle units according to the present invention. The particle units may contain these monomer units preferably in an amount of 0 to 99.5% by weight for those of (I), (II) and (III), 0 to 10% by weight, preferably 0 to 5% by weight, for those of (IV).

Among the polymer particle units forming the bound particulate structure of the present invention, typical examples of those having one kind of reactive groups are shown below, by which the present invention is not limited. The numerals in the brackets affixed to each exemplary compound indicate the weight percents of monomers employed in polymerization.

EXEMPLARY COMPOUNDS (1-1) Poly(styrene-co-glycidyl methacrylate) [90/10]
(1-2) Poly(styrene-co-methyl acrylate-co-glycidyl methacrylate) [80/15/5]
(1-3) Poly(styrene-co-n-butyl methacrylate-glycidyl methacrylate) [75/15/10]
(1-4) Poly(styrene-co-vinylbenzyl chloride-co-glycidyl methacrylate) [80/10/10]
(1-5) Poly(styrene-co-divinylbenzene-co-glycidyl acrylate) [90/2/8]
(1-6) Poly(p-vinyltoluene-co-glycidyl methacrylate) [90/10]
(1-7) Poly(methylmethacrylate-co-glycidyl methacrylate) [80/20]
(1-8) Poly(styrene-co-N,N-dimethylaminoethyl methacrylate) [95/5]
(1-9) Poly(styrene-co-aziridylethyl methacrylate) [95/5]
(1-10) Poly(styrene-co-methyl acrylate-co-acrolein) [90/5/5]
(1-11) Poly(styrene-co-acrylamide) [95/5]
(1-12) Poly(styrene-co-vinylthiol) [95/5]
(1-13) Poly(styrene-co-methylolacrylamide) [95/5]
(1-14) Poly(styrene-co-t-butylacrylate-glycidyl methacrylate) [95/5/5]
(1-15) Poly(styrene-co-vinylisocyanate) [95/5]
(1-16) Poly(methylacrylate-co-styrene-co-N-methylolacrylamide) [50/35/15]

Further, as another embodiment of the present invention, examples containing two or more kinds of monomer units different reactive groups in the same particle units are shown below.

EXEMPLARY COMPOUNDS (2-1) Poly(styrene-co-glycidyl methacrylate-co-N,N-dimethylaminoethyl methacrylate) [90/5/5]
(2-2) Poly(styrene-co-methacrylic acid-co-acrylamide) [95/2/3]
(2-3) Poly(styrene-co-N-methylolacrylamide-co-methoxyethyl acrylate) [90/5/5]
(2-4) Poly(p-vinyltoluene-co-N-methylolacrylamide-co-acrylic acid) [90/8/2]
(2-5) Poly(methyl methacrylate-co-glycidyl methacrylate-co-t-butyl acrylate) [80/10/10]
(2-6) Poly(styrene-co-p-vinylbenzyl chloride-co-acrylic acid-co-ethyl acrylate [75/10/5/10]
(2-7) Poly(styrene-co-methacrolein-co-2-hydroxyethyl methacrylate) [90/5/5]
(2-8) Poly(styrene-co-acrolein-co-acetoacetoxyethyl methacrylate) [85/5/10]
(2-9) Poly(styrene-co-N,N-dimethylaminoethyl acrylate-co-vinylsulfonylethyl methacrylate) [90/5/5]
(2-10) Poly(p-vinyltoluene-co-aminostyrene-co-vinylsulfonylethyl methacrylate) [85/10/5]

As still another embodiment of the present invention, there are shown below typical examples of combinations in which there are employed polymer particle units containing monomer units having one kind of reactive groups and polymer particle units containing monomer units having another kind of reactive groups different from said reactive groups, by which the present invention is not limited.

EXEMPLARY COMPOUNDS (3-1) Combination of:
a. Exemplary compound (1-1); and
b. Poly(styrene-co-N,N-dimethylaminoethyl methacrylate) [90/10]
(3-2)
a. Poly(styrene-co-acrylic acid) [97/3]
b. Poly(styrene-co-acrylamide) [97/3]
(3-3)
a. Exemplary compound (1-1)
b. Poly(p-vinyltoluene-co-tert-butyl acrylate) [95/5]
(3-4)
a. Poly(methyl acrylate-co-methacrylamide) [95/5]
b. Poly(styrene-co-N-methylolacrylamide) [95/5]
(3-5)
a. Poly(p-vinyl benzyl chloride-co-N-methylolacrylamide) [96/4]
b. Poly(styrene-co-itaconic acid) [98/2]
(3-6)
a. Exemplary compound (1-1)
b. Poly(styrene-co-tert-butyl acrylate) [92/8]
(3-7)
a. Poly(methyl acrylate-co-styrene-co-acrolein) [30/65/5]
b. Poly(methyl methacrylate-co-styrene-co-2-hydroxyethyl methacrylate) [25/70/5]
(3-8)
a. Poly(styrene-co-vinylsulfonylethyl acrylate) [80/20]
b. Poly(styrene-co-N,N-diethylaminomethyl acrylate) [97.5/2.5]
(3-9)
a. Poly(styrene-co-methyl acrylate-co-acetoacetoxyethyl acrylate) [90/5/5]
b. Exemplary compound (1-10)
(3-10)
a. Poly(styrene-co-methacrylic acid) [95/5]
b. Exemplary compound (1-1)

The above heat-stable organic polymer particle units can be produced by various conventional polymerization methods.

Typical addition polymerization methods may include solution polymerization (appropriate precipitation operation and, in some cases, crushing and particle classification operations are used for formation of said heat-stable particle units), suspension polymerization (sometimes referred to as pearl polymerization), emulsion polymerization, dispersion polymerization and precipitation polymerization. Preferably, suspension polymerization and emulsion polymerization are employed.

In the following, Synthetic examples of the exemplary compounds of the present invention are shown, but the present invention is not limited thereby.

SYNTHESIS EXAMPLE 1

Synthesis of the exemplary compound (1-1)

A mixture of monomers comprising 90 parts of styrene, 10 parts of glycidyl methacrylate, and 3 parts of 2,2'-azobis(2,4-dimethylvaleronitrile) and a polymerization initiator was added into 700 ml of an aqueous solution of 3% by weight of tricalcium phosphate and 0.04% by weight of sodium dodecylbenzene sulfonate based on the above monomers, while stirring the mixture at a stirring speed of 5000 r.p.m. by means of a TK-homojetter (produced by Tokushu Kika Kogyo). After completion of the addition, the mixture was further continued to be stirred for about 30 minutes until the particle sizes became about 20 microns as observed by a microscope, whereupon the mixture was transferred into a four-necked flask equipped with a conventional stirrer (anchor type), a cooling tube, a nitrogen gas inlet tube and a thermometer. The stirring speed was changed to 200 r.p.m., and polymerization was carried out at 60° C. under a nitrogen gas stream for 8 hours to complete the reaction. Then, the contents were cooled to room temperature and tricalcium phosphate was removed by decomposition with a dilute aqueous hydrochloric acid solution. The residual mixture was washed repeatedly with water and thereafter the polymer particles were separated by separation, followed by drying, to obtain polymer particle units with an average particle diameter of 18 microns.

SYNTHESIS EXAMPLE 2

Synthesis of the exemplary compound (1-3)

A mixture of monomers comprising 75 parts of styrene, 15 parts of n-butyl methacrylate, 10 parts of glycidyl methacrylate and 3 parts of 2,2'-azobis(2,4-dimethylvaleronitrile) and a polymerization initiator was added to 700 ml of an aqueous solution of 2% by weight of tricalcium phosphate and 0.02% by weight of sodium dodecylbenzene sulfonate based on the above monomers, while stirring the mixture at a stirring speed of 2000 r.p.m. by means of a TK-homojetter. After completion of the addition, the mixture was further continued to be stirred for 30 minutes until the particle sizes of the droplets of the monomer mixture became about 100 microns, whereupon the reaction and the procedures as described in Synthetic example 1 were repeated, to provide polymer particle units with an average particle diameter of 100 microns.

SYNTHESIS EXAMPLE 3

Synthesis of the exemplary compound (3-8) b

A monomer mixture was prepared by dissolving 3 parts of 2,2'-azobis(2,4-dimethylvaleronitrile) in 97.5 parts of styrene and 2.5 parts of N,N-dimethylaminomethyl methacrylate. Subsequently, there were prepared 700 ml of an aqueous solution of 3% by weight of a hydrophilic silica-Aerozil 200 (produced by Tegusa Co.) based on the above monomers, and the above monomer mixture was added into said aqueous solution, while stirring the solution at 6000 r.p.m. by means of a TK-homojetter. After completion of the addition, the mixture was stirred for about 30 minutes until being dispersed to liquid droplets of about 20 microns, as observed by a microscope, and then the dispersion was charged into a four-necked flask equipped with a conventional stirring device (anchor type), a cooling tube, a nitrogen gas inlet tube and a thermometer. Polymerization was carried out under a nitrogen gas stream, at a stirring speed of 250 r.p.m. at 60° C. for 8 hours to complete the reaction. The contents were then cooled to room temperature, washed with a dilute aqueous sodium carbonate solution, then with water repeatedly, followed by filter-off and drying of the polymer, to provide polymer particle units with an average diameter of 16.5 microns.

SYNTHESIS EXAMPLE 4

Synthesis of the exemplary compound (3-10) a

A monomer mixture was prepared by dissolving 3 parts of 2,2'-azobis(2,4-dimethylvaleronitrile) in 95 parts of styrene and 5 parts of methacrylic acid. Subsequently, there was prepared 700 ml of an aqueous solution of 3% by weight of aluminum oxide (produced by Tegusa Co.) based on the above monomers, and the above monomer mixture was added to said aqueous solution, while stirring the solution at 6000 r.p.m. by means of a TK-homojetter. After completion of the addition, stirring was continued at the same speed for about 30 minutes until the dispersion was effected to liquid droplets of about 15 microns, as observed by a microscope, and then the reaction and the procedures as described in Synthesis example 3 were repeated, to provide polymer particle units with an average diameter of 16 microns.

The above heat-stable polymer particle units containing the reactive groups according to the present invention have a glass transition temperature (hereinafter abbreviated as $T_g$), typically of 30° C. or higher, preferably a $T_g$ of 40° C. or higher. The term "$T_g$" mentioned in the present specification means a temperature at which the polymer undergoes change in state from a glassy state to a rubbery state, and may be contemplated as an index for heat stability of the polymer. The $T_g$ of a polymer can be measured according to the method as described in, for example, "Techniques and Methods of Polymer Evaluation" Vol. 1, Marcel Dekker, Inc., N.Y. (1966).

Various methods can be employed for preparing the bound particulate structure zone of the present invention. One of the preferable methods comprises the following steps, namely:

(1) preparing a stable dispersion of the heat-stable organic polymer particle units containing the reactive groups in a liquid carrier which does not dissolve said particles, (2) applying this stable dispersion to a support and (3) removing the carrier at a temperature below the heat-stability temperature of said organic polymer particle units, while permitting the reactive groups of said particle units to be chemically bound with each other.

The term "stable dispersion" means that the particle units remain admixed in the carrier without forming an agglomerated mass of particle units. Dispersions useful in preparing the bound particulate structure zone should remain stable for a time sufficient to apply them to a support.

To form such stable dispersions, a wide variety of techniques can be used individually or in combination.

One useful technique comprises the addition of a surfactant to the liquid carrier to facilitate distribution and stabilization of the particle units in the dispersion.

Representative surfactants which can be employed include Triton X-100 ® (octylphenoxy polyethoxyethanol from Rohm and Hass) and Surfactant 10G® (nonylphenoxy-polyglycidol from Olin Corp.).

The above surfactant may be employed in an amount which can be selected from a wide range, but generally 10% by weight to 0.005% by weight, preferably 6% by weight to 0.05% by weight, based on the weight of the polymer particle units. As alternative techniques, there are procedures such as sonication treatments, physical blending and agitation treatments and pH adjustments. These techniques can be more useful when combined with the technique as described above.

The particle units of the present invention can be prepared by permitting the reactive groups contained in said particle units to be chemically bound with each other when removing the liquid carrier in the dispersion to give a bound particulate structure zone. It is useful to incorporate a catalyst such as an acid or an alkali to promote chemical bonding in the dispersion. In particular, among the acid catalysts, a volatile acid catalyst (e.g., acetic acid) is very useful. The procedure for removing the liquid carrier may be practiced desirably at a temperature below the heat-stability temperature of the organic polymer particle units, preferably at 10° to 70° C.

As the liquid carrier in the aforesaid dispersion, there may be employed an aqueous liquid. But other liquid carriers such as organic liquids may also be available, provided that said particle units are insoluble in the carrier so that their particulate character can be retained.

Representative liquid carriers other than water may include water-miscible organic solvents, mixtures of water with water-miscible organic solvents and appropriate water-immiscible organic solvents. Examples of water-miscible organic solvents are lower alcohols (namely, alcohols with alkyl groups having 1 to 4 carbon atoms), acetone and tetrahydrofuran. As the water-immiscible solvents, there may be mentioned lower alkyl esters such as ethyl acetate and halogenated organic solvents such as halogenated hydrocarbons (e.g., chloroform, methylene chloride and carbon tetrachloride).

The bound particulate structure zone of the present invention can advantageously contain one or more interactive compositions. These compositions contain one or more active components that undergo interaction with an analyte, or a reaction or decomposition product of the analyte, or with each other upon application of a liquid sample containing the analyte to an analytical element incorporating the bound particulate structure zone. Such interaction can cause the release of a preformed detectable species within the element, the formation of a detectable species or otherwise produce a detectable change in the element.

The term "interaction" is meant to refer to chemical activity, catalytic activity (as in the formation of an enzyme-substrate complex), immunogenic activity (as in an antigen-antibody reaction) and any other form of electrical, chemical or physical interaction.

These electrical chemical or physical interactions can release, produce, or otherwise provide within the element a detectable change. The aforesaid change is directly or indirectly indicative of the presence and/or concentration of a desired analyte, or a reaction or decomposition product of the analyte.

Preferably, the detectable change that is produced is radio-metrically detectable. Radiometric detection refers to detection by use of electromagnetic radiation measuring techniques such as fluorimetry, colorimetry, radioactive counting, and phosphorimetry.

As will be appreciated, among the various components that can be present in interactive composition are colorimetrically detectable dyes, pigments, and complexes; fluorimetrically detectable dyes, pigments and complexes; phosphorescent tags; radioactive tags; chemical reagents; antigens; haptens; immunoreagents such as antibodies and antigen-antibody complexes; enzymes; and precursors of the foregoing components.

For further detail with respect to use of these components, reference may be made to U.S. Pat. No. 3,992,158; Belgian Pat. No. 862,955 and EPC Publication No. 0002963.

If the interactive compositions are present in the bound particulate structure zone, they can be immobilized therein to minimize or prevent undesired migration of the composition within the zone or other zones of an element containing said zone. Immobilization can be effected by a variety of means including physical adsorption and chemical bonding to the said particles.

For example, in the chemical bonding method, the monomer units containing the reactive groups to be contained in said particle units of the present invention can be advantageously used. With the use of such monomer, immobilization can readily be attained by chemical bonding between the interactive composition and the free reactive groups which have not participated in the chemical bonding between said particle units in the area of contact. In other cases, the molecular size or configuration of the interactive composition may be effective to physically entrap and immobilize a particular interactive composition in the bound particulate structure zone without use of any special physical adsorption or chemical fixing technique.

The analytical elements according to the present invention containing the aforesaid bound particulate structure zone can have any one of a variety of different configurations. It may have one or more of the bound particulate structure zones of the present invention, or alternatively a suitable combination of the bound particulate structure zone with any of a variety of functional zone, reagent containing zones and members, as exemplified by the reagent zone, the filtration zone, the reflection zone and the subbing zone as disclosed in U.S. Pat. No. 3,992,158, the radiation-blocking zone as disclosed in U.S. Pat. No. 4,042,335, the barrier zone as disclosed in U.S. Pat. No. 4,066,403, the registration zone as disclosed in U.S. Pat. No. 4,144,306, the migration-inhibition zone as disclosed in U.S. Pat. No. 4,166,093, the scintillation zone as disclosed in U.S. Pat. No. 4,127,499, the scavenger zone as disclosed in Japanese Provisional Patent Publication No. 90859/1980 and the destructive pod-shaped member as disclosed in U.S. Pat. No. 4,110,079, to constitute the analytical element adpated to accomodate the object of the present invention.

The techniques for preparation of the above-mentioned zones and the techniques for assembling the above-mentioned zones in the analytical element of the present invention may be the same as or similar to those disclosed in the above-mentioned Patents. There are also detailed description in the above-mentioned Patents about the useful materials that may be employed for preparation of such zones.

Except for reflecting and radiation-blocking agents or zones that may be present in elements of the invention, the various zones, supports, and other layers can be "radiation-transmissive". In the present specification, the term "radiation-transmissive" refers to zones, supports and materials in an element that permit effective passage of electromagnetic radiation used to detect an analytical change produced in the element. Such radiation can include visible light, fluorescent emission, radioactive radiation and X-ray radiation. The choice of a particular "radiation-transmissive" material in any given instance will depend upon the particular radiation used.

Of course, radiation-transmissive materials are not required in the present invention. In various embodiments, one may choose to use radiation-blocking agents or zones to prevent radiation from interfering with chemical interactions occurring within the element.

As such a radiation-blocking agent, there may be mentioned the following.

As radiation-blocking agents for visible ray, there may be mentioned such a white pigment as titanium dioxide, barium sulfate and the like.

As radiation-blocking agents for fluorometric detection, there may be mentioned, for example Wachtung (Wachtong) Red B Pigment ® (from E. I. du Pont de Nemours), Regal 300 ® (from Cabot), Permanent Purple ® (from GAF), Paliofast Blue ® (from BASF), Sol Fast Methyl Violet ® (from Sherwin Williams), and as radiation-blocking agents for X-ray analysis, there may be mentioned conventionally known inorganic compounds and so on. Such radiation-blocking agents are usually contained in the polymer particle units according to this invention in an amount of 0.5 to 60% by weight.

As noted above, the various zones are in fluid contact with one another. In the present specification the term "fluid contact" refers to zones which are associated with one another in a manner such that, under conditions of use, a fluid (whether liquid or gaseous) can pass from one to the other. Such fluid contact capability is preferably uniform along the contact interface between the fluid contacting zones. Zones which are in fluid contact may be contiguous, but they also may be separated by intervening zones. Such intervening zones, however, will also be in fluid contact and will not prevent the passage of fluid. In some circumstances, it may be desirable to use zones that are initially spaced apart within an element. In such case, fluid contact between such zones is achieved substantially at the time of sample application, as by compressing the element.

As previously mentioned, the elements of the present invention can be carried on a support. Useful support materials include polymeric materials such as cellulose acetate, poly(ethylene terephthalate), polycarbonates and polyvinyl compounds (such as polystyrenes), glass, metal and paper. A support of choice for any particular element will be compatible with the intended mode of result detection.

For example, for fluorimeteric detection wherein fluorimetric emission within the element is detected as the emission is transmitted from within the element through the support to an external detector, it is desirable to employ as a support material a material which exhibits a low degree of background fluorimetric emission.

When an element does include a support, the reagent zone, the reflecting or radiation-blocking zone, and the registration zone, will usually, but not necessarily, be interposed in the element between the support and the bound particulate structure of the present invention.

In preparing the analytical element of this invention, the individual zones can be preformed and thereafter laminated prior to use or maintained as separate zones until brought into fluid contact with the element is placed in use. Zones preformed as separate members, if coatable, can advantageously be coated from solution or dispersion on a surface from which the zone can be physically stripped when dried. However, a convenient procedure which can avoid problems of multiple stripping and lamination steps when contiguous zones are desired, is to coat an initial zone on a stripping surface or a support, as desired, and thereafter to coat successive zones directly on or beside those previously coated.

The analytical element having the bound particulate structure zone of this invention can be coated by the dip coating method, the air knife method, the curtain coating method or the extrusion coating method with the use of a hopper as disclosed in U.S. Pat. No. 2,681,294. If desired, it is also possible to use the method as disclosed in U.S. Pat. No. 2,761,791 and U.K. Pat. No. 837,095 for simultaneous coating of two or more layers.

Elements of the present invention can be adapted for use not only in the field of clinical chemistry, but in other fields of chemical analysis. In addition, by utilizing the function of holding a certain amount of liquid within a certain area of the film, the element of the present invention can be associated with other functional zones (e.g., layers of photographic elements).

Analytical elements of the present invention are very advantageous for use in clinical testing of body fluids, such as blood, blood serum, lymph and urine. In particular, blood serum is conventionally used in analysis of blood. But the analytical element can be conveniently applicable for analysis of any of whole blood, blood serum and blood plasma.

When whole blood is used, a radiation-blocking zone or other reflecting zone may be provided, if necessary, in order to avoid interference of detecting radiation by the blood cells. Of course, if it is desired to observe directly the color of blood cells directly, such as in a haemoglobin analysis, no such reflecting layer is necessary.

After the analytical result is obtained as a detectable change, by use of the analytical element of the present invention, it is measured by reflection spectrophotometry, transmission spectrophotometry, fluorescence spectrophotometry or scintillation counting, corresponding the various detectable changes. The thus obtained values of measurement can be utilized for determination of the unknown quantity of analyte with reference to the calibration curve previously prepared.

Immunoassay is a well-recognized technique for qualitative or quantitative assay of antibodies and antigens. The basis for all immunoassay techniques is the unique, immunological phenomenon whereby a specific antibody recognizes and binds to a specific antigen.

Typical examples of immunoassay are radioimmunoassay, enzymeimmunoassay and fluorescenceimmunoassay.

The antibodies, antigens to be used in these immunoassays and preparation techniques of label antigens or label antibodies, immunoassay techniques and principles are described in detail in textbooks, such as "Radioimmunoassay" ed. by Minoru Irie, Kodansha (1974), "Enzymeimmunoassay" ed. by Eiji Ishikawa, Tadashi Kawai & Kiyoshi Miyai, Igaku Shoin (1978).

Most currently available techniques for performing the immunoassay as mentioned above suffer from various disadvantages as shown below:

(I) Relatively large volumes (0.1 to 1.0 ml) of test liquid may be necessary compared to conventional chemical and blood assays typically using 10 to 200 μl of liquid sample.

(II) Time-consuming incubation (several hours or overnight) of the test mixture is required.

(III) After incubation, it is necessary to perform physical separation of bound antigen-antibody conjugate and unbound antigens or antibodies.

(IV) Many steps are necessary and must be performed individually and separately for completion of the assay (including sample addition, incubation, separation, quantitation of label).

But the use of the analytical element of this invention to conduct immunoassay overcomes many of the above drawbacks. It will be understood, however, that other than the immunoassay based on the antigen-antibody reaction as mentioned above, as immunoassay based on an antigen-antibody displacement interaction as described in German OLS No. 28 01 455 is also applicable for the analytical element of the present invention.

In addition, an amount of the antibody for the labelled antigen is incorporated and immobilized in an analytical element, preferably within a zone thereof having a coherent particulate structure zone. Such immobilization can be accomplished by adsorption or chemical bonding to the surface of the organic polymer particle units of the bound particulate structure. The liquid sample to be analyzed for unknown antigen is then brought into contact with the element in the presence of the labelled antigen. The labelled antigen can be associated with the immunoassay element in one of several ways including, among others:

(1) direct addition of the labelled antigen to the liquid sample (containing unlabelled antigen) which is then applied to the immunoassay element for analysis;

(2) separate addition of the labelled antigen and the liquid sample to the immunoassay element including (a) addition of the labelled antigen just prior to or after addition of the liquid sample as well as (b) addition of the labelled antigen to the element followed by drying and then rewetting the element upon addition of the liquid sample; or (3) incorporation of the labelled antigen in the immunoassay element so that analysis can be initiated simply by application of the liquid sample.

For example, the labelled antigen can be incorporated in a separate reagent zone of the element or the same zone of the element containing the immobilized antibody. In any case, when the labelled antigen is incorporated in the element, care should be taken to maintain the labelled antigen apart from the immobilized antibody so that premature binding of labelled antigen to antibody is avoided.

When the liquid sample is brought into contact with the immunoassay element in the presence of the associated, labelled antigen as noted above, the labelled antigen and the unlabelled antigen (present in the sample and representing the unknown to be determined) compete for binding to the antibody which is present immobilized in one zone of the element. Useful methods of measurement to determine the presence and/or concentration of unlabelled antigen that can then be employed include: (A) detecting the amount of unbound, labelled antigen that has migrated into a second zone of the element, e.g., a registration zone, said amount being proportional to the amount of analyte present in said sample; or (B) detecting the amount of bound, labelled antigen which binds to the immobilized antibody, said amount being inversely proportional to the amount of analyte present in said sample. In either method, the amount of unlabelled antigen (i.e., the analyte) in the liquid sample can be determined based on the detected concentration of labelled antigen.

The present invention is illustrated in further detail by referring to the following Examples, by which the present invention is not limited at all.

EXAMPLE 1

On a transparent poly(ethyleneterephthalate) support of a film thickness of about 180 microns which had been subjected to undercoating, there was coated a layer of deionized gelatin to a thickness of about 20 microns of dried film. On several samples of the thus coated support, there were further provided upper layers of the bound particulate structure zones of the present invention having the compositions as shown in Table-1-1 and porous spreading (developing) zones for comparative purpose, respectively, to form elements I, II, III, IV and comparative elements I and II, respectively.

TABLE 1-1

| No. | Compositions of bound particulate structure zones and porous spreading zones |
|---|---|
| Element I | Bound particulate structure zone with a thickness of 280 microns of dried film consisting of 15.0 g/dm$^2$ of particle units of the exemplary compound (1-1) of the present invention with an average particule diameter of about 20 microns. |
| Element II | Bound particulate structure zone with a thickness of 280 microns of dried film consisting of 15.0 g/dm$^2$ of particle units of the exemplary compound (1-12) of the present invention with an average particle diameter of about 18 microns. |
| Element III | Bound particulate structure zone with a thickness of 280 microns of dried film consisting of 15.0 g/dm$^2$ of particle units of the exemplary compound (2-1) of the present invention with an average particle diameter of about 20 microns. |
| Element IV | Bound particulate structure zone with a thickness of 280 microns of dried film consisting of each 7.5 g/dm$^2$ of particle units of the exemplary compounds (3-7) a. and b. of the present invention with an average diameter of about 20 microns. |
| Comparative element I | Porous spreading zone with a thickness of 150 microns of dried film disclosed in U.S. Pat. No. 3,992,158, consisting of 0.3 g/dm$^2$ of titanium dioxide and 0.037 g/dm$^2$ of cellulose diacetate. |
| Comparative element II | Porous spreading zone disclosed in U.S. Pat. No. 3,992,158, consisting of 6.5 g/dm$^2$ of inert glass beads with an average particle diameter of about 20 microns and 0.13 g/dm$^2$ of deionized gelatin. |

The following tests were conducted for the elements according to the present invention and comparative elements as shown in the above Table-1-1.

That is, peel-off strength was tested for each of the elements by adhering a strip of Cellophane tape with a length of 5 cm on the bound particulate structure zone and the porous spreading zone of the above elements and stripping off the adhered tape by holding one end thereof. Depending on the degree of peel-off, peel-off strength was rated according to the following ranks:

| | |
|---|---|
| No peel-off at all | A |
| Peel-off of half or less of the portion adhered with Cellophane tape | B |
| Peel-off of all of the portion adhered with Cellophane tape | C |
| Peel-off of more than the portion adhered with Cellophane tape | D |

Further, on the bound particulate structure zone and the porous spreading zone of the same elements and comparative elements, respectively, 10 µl of a liquid sample colored by addition of 0.05% by weight of a red pigment (Brilliant Scarlet 3 R) to human serum was added dropwise, and the time needed for taking up the liquid sample into the zone and the change in form of the zone were observed, to give the results as shown in Table-1-2.

TABLE 1-2

| No. | Peel-off test | Time for take-up (seconds) | Change in form of zone |
|---|---|---|---|
| Element I | A | 8 | None |
| Element II | A | 6 | None |
| Element III | A | 8 | None |
| Element IV | A | 9 | None |
| Comparative element I | D | 36 | None |
| Comparative element II | C | 58 | zone disintegrated 10 seconds after dropwise addition |

As apparently seen from the results as sown in Table-1-2, the Comparative elements I and II are both brittle in mechanical strength. Particularly, in case of Comparative element II, it can fulfill no sufficient function of transporting a liquid sample, since it cannot maintain the structure of porous spreading zone by application of a liquid sample.

In contrast, the elements I to IV having the bound particulate structure zone of the present invention have interconnected voids for transport of a liquid sample and are also great in their mechanical strengths, thus enabling taking-up of a liquid sample within a very short period of time.

EXAMPLE 2

On a transparent poly(ethyleneterephthalate) support with a film thickness of 180 microns, which had been subjected to undercoating, there were applied coatings successively of reagent zone for assay of glucose and of radiation-blocking zone, having the compositions, respectively, as shown below.

(1) Reagent zone for assay of glucose comprising the following components and adjusted to pH 7.0 with an aqueous 5% sodium hydroxide solution:
Glucose oxidase: 240 U/dm$^2$
4-Aminoantipyrene hydrochloride: 0.0086 g/dm$^2$
1,7-Dihydroxy naphthalene: 0.0065 g/dm$^2$
Peroxidase: 180 U/dm$^2$
5,5-Dimethyl-1,3-cyclohexadione: 0.0022 g/dm$^2$
6-Amino-4,5-dihydroxy-2-methylpyrimidine: 0.0002 g/dm$^2$
3,3-Dimethylglutaric acid: 0.0196 g/dm$^2$
Deionized gelatin: 0.196 g/dm$^2$ (2) Radiation-blocking zone comprising the following components:
Titanium dioxide: 1.8 g/dm$^2$
Triton X-100 (octylphenoxypolyethoxy ethanol, produced by Rohm and Haas): 0.108 g/dm$^2$
Poly(acrylamide-co-ethylacryloyl acetate) [weight ratio: 90/10]: 0.108 g/dm$^2$ On the film thus prepared, each of the bound particulate structure zone and the porous developing zone were laminated to provide the analytical element I of the present invention and the comparative analytical element I, respectively.

TABLE 2

| Analytical element | Compositions of the bound particulate structure zone and the porous spreading zone |
|---|---|
| Analytical element I of the invention | Bound particulate structure zone with a thickness of 280 microns of dried film consisting of 15.0 g/dm$^2$ of particle units of the exemplary compound (1-1) of the present invention with an average particle diameter of about 20 microns and 0.3 g/dm$^2$ of Surfactant 10 G ® (p-nonylphenoxy polyglycidol, produced by Olin Corp.) |
| Comparative analytical element I | Porous spreading zone disclosed in U.S. Pat. No. 3,992,158, consisting of 0.3 g/dm$^2$ of titanium dioxide, 0.037 g/dm$^2$ of cellulose diacetate and 0.01 g/dm$^2$ of Surfactant 10 G (the same as above) |

As the next step, on each of the above elements, 10 µl each of commercially available serum solutions for calbration with glucose concentrations of 0 to 400 mg/dl were added dropwise and incubation was carried out for 10 minutes in each case, followed by measurement of the reflection density of the dye formed in the reagent zone through a transparent poly(ethyleneterephthalate) support, to prepare a calibration curve.

Then, 10 µl each of various human blood serum samples and human whole blood samples (each containing an unknown glucose level) added dropwise to each element, and glucose concentration was determined in each case from the calibration curve previously prepared.

As a Control method, glucose concentrations in similar samples were also determined by means of Glucose B-test-Wako (a kit for assay of glucose by Trimder method, produced by Wako Junyaku Co.)

As the result, when human blood serum was applied, both of the analytical element I of the invention and the comparative example I were found to exhibit similar good relationships with the Control method. But, when human whole blood was applied, the blood cells in whole blood caused clogging in the voids in the porous spreading zone, resulting in inhibition of serum flow in the whole blood sample, indicating only abnormal values of analytical measurement observed showing no relationship as compared with the analytical values measured by the Control method.

In contrast, as the result of similar analysis by the analytical element of the present invention, the glucose concentration exhibited good relationship with the value of the Control method, indicating that the analytical element of the present invention can make avail of a whole blood sample.

EXAMPLE 3

On a polystyrene support showing only a low level of fluorescence, there were coated successively the zones having the following compositions:

(1) Bound particulate structure zone for detection coated after adjustment of the composition including the following components to pH 7.2 with a phosphate buffer:

Polymer particle units of the exemplary compound (1-1) of the present invention with an average particle diameter of 8 to 10 microns, to which normal rabbit serum was adsorbed: 4.1 g/dm$^2$ Nonionic surfactant Zeonil FSN (produced by E. I. Du Pont de Nemours & Co.): 0.016 g/dm$^2$ (2) Bound particulate structure zone containing interactive composition coated after adjustment of the composition including the following components to pH 7.2 with a phosphate buffer:

Polymer particle units of the exemplary compound (1-1) of the present invention with an average particle diameter of 8 to 10 microns, comprising Wachtong Red B Pigment (produced by E. I. Du Pont de Nemours & Co.) as a radiation-blocking agent in an amount of 2% by weight to which rabbit α-fetoprotein antibody was adsorbed: 1.4 g/dm$^2$ Nonionic surfactant Zeonil FSN (produced by E. I. Du Pont de Nemours & Co.): 0.014 g/dm$^2$ For the immunoassay element for assay of α-fetoprotein of the present invention prepared according to the above procedures, the following test serum was applied. That is, in 10 μl of a serum prepared by removing α-fetoprotein from a normal human adult serum with the use of an immunoadsolvent, $5 \times 10^{-8}$ mole of fluorescent labelled α-fetoprotein as labelled antigen and 0 to $1 \times 10^{-5}$ various concentrations of α-fetoprotein were contained to prepare test serums, and each 10 μl thereof was added dropwise onto the above immunoassay element of the present invention.

The 10 μl of the test serum was absorbed into the bound particulate structure zone containing the interactive composition all within 15 seconds. Then, the above element was subjected to incubation at 37° C. for 20 minutes. Subsequently, the intensity of fluorescence of unbound labelled α-fetoprotein was measured for each element through the polystyrene support by means of a reflection fluorescentphotometer having an excitation filter and an emission filter at 490 nm and 515 nm. The results are shown in Table 3.

TABLE 3

| α-fetoprotein concentration in test serum | Intensity of fluorescence measured (optional units) |
| --- | --- |
| 0 | 355 |
| $2 \times 10^{-8}$ mole | 369 |
| $6 \times 10^{-8}$ mole | 442 |
| $1 \times 10^{-7}$ mole | 470 |
| $1 \times 10^{-6}$ mole | 530 |
| $1 \times 10^{-5}$ mole | 580 |
| Blank with a phosphate buffer | 45 |

As apparently seen from Table 3, the immunoassay element of the present invention enables rapid immunoassay by measurement of fluorescence corresponding to unlabelled α-fetoproteins with various concentrations contained in test serums.

We claim:

1. In an analytical element for the determination of the presence of an analyte in a liquid containing the same, said analytical element having an interconnected void structure zone positioned on one side of a liquid-impermeable, light-transmissive support, the improvement comprising:

said interconnected void structure zone comprising a plurality of heat-stable organic polymer particle units having reactive groups and having a particle size of from 1 to 350 microns, said particle units being chemically bonded directly to each other through said reactive groups, said particle units being arranged in the form of a bound particulate structure having a three-dimensional lattice, said bound particulate structure being non-swellable in said liquid and having interconnected voids wherein the void volume of said bound particulate structure is between 25 and 85% to thereby permit said liquid to permeate therethrough.

2. The analytical element of claim 1, wherein the element contains an immunoreagent.

3. The analytical element of claim 1, wherein the particle units contain a colorant.

4. The analytical element of claim 1, wherein said analyte is a complete cellular structure and said organic polymer particle unit has a particle size of 20 to 150 microns.

5. The analytical element of claim 1, wherein said analyte is a macromolecule and said organic polymer particle unit has a particle size of 2 to 50 microns.

6. The analytical element of claim 1, wherein said bound particulate structure is non-swellable in an aqueous liquid.

7. The analytical element of claim 1, wherein the organic polymer units contain at least two different polymer units having different monomer units and different reactive groups.

8. The analytical element of claim 7, wherein the organic polymer units comprise combinations selected from the group consisting of:

(A) a. Poly(styrene-co-glycidyl methacrylate) 90/10 and
 b. Poly(styrene-co-N,N—dimethylaminoethyl methacrylate) 90/10;
(B) a. Poly(styrene-co-acrylic acid) 97/3 and
 b. Poly(styrene-co-acrylamide) 97/3;
(C) a. Poly(styrene-co-glycidyl methacrylate) 90/10 and
 b. Poly(p-vinyltoluene-co-tert-butyl acrylate) 95/5;
(D) a. Poly(methyl acrylate-co-methacrylamide) 95/5 and
 b. Polystyrene-co-N—methylolacrylamide) 95/5;
(E) a. Poly(p-vinylbenzyl chloride-co-N—methylolacrylamide) 96/4 and
 b. Poly(styrene-co-itaconic acid) 98/2;
(F) a. Poly(styrene-co-glycidyl methacrylate) 90/10 and
 b. Poly(styrene-co-tert-butyl acrylate) 92/8;
(G) a. Poly(methyl acrylate-co-styrene-co-acrolein) 30/65/5 and
 b. Poly(methyl methacrylate-co-styrene-co-2-hydroxyethyl methacrylate) 25/70/5;
(H) a. Poly(styrene-co-vinylsulfonylethyl acrylate) 80/20 and
 b. Poly(styrene-co-N,N—diethylaminomethyl acrylate) 97.5/2.5;
(I) a. Poly(styrene-co-methyl acrylate-co-acetoacetoxy-

| | |
|---|---|
| | -continued |
| | ethyl acrylate 90/5/5 and |
| | b. Poly(styrene-co-methyl acrylate-co-acrolein) 90/5/5; |
| (J) | a. Poly(styrene-co-methacrylic acid) 95/5 and |
| | b. Poly(styrene co-glycidyl methacrylate) 90/10 | wherein the percent by weight of the monomers forming said organic polymer units is expressed numerically.

9. The analytical element of claim 1, wherein the element contains an interactive composition containing at least one component which undergoes an interaction with said analyte or a reaction or decomposition product thereof.

10. The analytical element of claim 9, wherein the organic polymer particle units contain reactive groups, which do not participate in the chemical bonding between the units, for chemical attachment to said interactive composition.

11. The analytical element of claim 1, wherein the particle units are solid particles of substantially uniform size.

12. The analytical element of claim 12, wherein the particles are in the form of spherical beads.

13. The analytical element of claim 1, wherein the organic polymer particle units comprise a copolymer having at least one monomer having reactive groups and at least one monomer selected from the group consisting of monomers having the formula

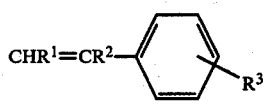   (I)

wherein each of $R^1$ and $R^2$, which can be the same or different, is a non-interfering substituent selected from the group consisting of a hydrogen atom, a halogen atom, an amino-free alkyl group, a substituted amino-free alkyl group, an amino-free aryl group, and a substituted amino-free aryl group having 1 to 10 carbon atoms and $R^3$ is selected from the group consisting of a hydrogen atom, a halogen atom, an amino-free aliphatic group, a substituted amino-free aliphatic group, an amino-free aromatic group and a substituted amino-free aromatic group having 1 to 10 carbon atoms; monomers having the formula $$CHR^6=CR^4-COOR^5$$   (II)

wherein $R^6$ has the same meaning as $R^1$ in the formula (I), $R^4$ is a hydrogen atom or a methyl group and $R^5$ is selected from the group consisting of an aryl group, an alkyl group, an alkaryl group and an aralkyl group, each having 1 to 10 carbon atoms;

(III) a polymerizable unsaturated nitrile monomer; and (IV) an interparticle crosslinking monomer having two addition-polymerizable groups.

14. The analytical element of claim 13, wherein the copolymer comprises 0.1 to 30% by weight of the monomer having reactive groups, 0 to 99.5% by weight of the monomer (I), 0 to 99.5% by weight of the monomer (II), 0 to 99.5% by weight of the monomer (III) and 0 to 10% by weight of the monomer (IV).

15. The analytical element of claim 14, wherein the copolymer is selected from the group consisting of:

(a) Poly(styrene-co-glycidyl methacrylate) 90/10
(b) Poly(styrene-co-methyl acrylate-co-glycidyl methacrylate) 80/15/5
(c) Poly(styrene-co-n-butyl methacrylate-co-glycidyl methacrylate) 75/15/10
(d) Poly(styrene-co-vinylbenzyl chloride-co-glycidyl methacrylate) 80/10/10
(e) Poly(styrene-co-divinylbenzene-co-glycidyl acrylate) 90/2/8
(f) Poly(p-vinyltoluene-co-glycidyl methacrylate) 90/10
(g) Poly(methyl methacrylate-co-glycidyl methacrylate) 80/20
(h) Poly(styrene-co-N,N-dimethylaminoethyl methacrylate) 95/5
(i) Poly(styrene-co-aziridylethyl methacrylate) 95/5
(j) Poly(styrene-co-methyl acrylate-co-acrolein) 90/5/5
(k) Poly(styrene-co-acrylamide) 95/5
(l) Poly(styrene-co-vinylthiol) 95/5
(m) Poly(styrene-co-methylolacrylamide) 95/5
(n) Poly(styrene-co-t-butyl acrylate-co-glycidyl methacrylate) 95/5/5
(o) Poly(styrene-co-vinylisocyanate) 95/5
(p) Poly(methyl acrylate-co-styrene-co-N-methylolacrylamide) 50/35/15
(q) Poly(styrene-co-glycidyl methacrylate-co-N,N-dimethylaminoethyl methacrylate) 90/5/5
(r) Poly(styrene-co-methacrylic acid-co-acrylamide) 95/2/3
(s) Poly(styrene-co-N-methylolacrylamide-co-methoxyethyl acrylate) 90/5/5
(t) Poly(p-vinyltoluene-co-N-methylolacrylamide-co-acrylic acid) 90/8/2
(u) Poly(methyl methacrylate-co-glycidyl methacrylate-co-t-butyl acrylate) 80/10/10
(v) Poly(styrene-co-p-vinylbenzyl chloride-co-acrylic acid co-ureidoethyl acrylate) 75/10/5/10
(w) Poly(styrene-co-methacrolein-co-2-hydroxyethyl methacrylate) 90/5/5
(x) Poly(styrene-co-acrolein-co-acetoacetoxyethyl methacrylate) 85/5/10
(y) Poly(styrene-co-N,N-dimethylaminoethyl acrylate-co-vinylsulfonylethyl methacrylate) 90/5/5
(z) Poly(p-vinyltoluene-co-aminostyrene-co-vinylsulfonylethyl methacrylate) 85/10/5 wherein the percent by weight of the monomers forming said copolymers is expressed numerically.

16. The analytical element of claim 1, wherein the organic polymer particle units contain 0.1 to 30% by weight of monomers having reactive groups.

17. The analytical element of claim 16, wherein the organic polymer particle unit contain 0.5 to 20% by weight of monomers having reactive groups.

18. The analytical element of claim 1, 16 or 17, wherein the bound particulate structure is formed through chemical bonding between the same reactive groups.

19. The analytical element of claim 18, wherein the reactive groups are selected from the group consisting of epoxy, aziridyl, formyl, hydroxymethyl, isocyanate, thiol and carbamoyl groups.

20. The analytical element of claim 1, 16 or 17, wherein the bound particulate structure is formed through chemical bonding between different reactive groups.

21. The analytical element of claim 20, wherein the reactive groups are selected from combinations from the group consisting of epoxy and amino, carbamoyl and hydroxymethyl, carbamoyl and methoxy, hydroxymethyl and carboxymethoxymethyl, hydroxyl and carboxyl, epoxy and —COOC$_4$H$_9$(t), ureido and carboxyl, formyl and hydroxyl, vinylsulfonyl and amino, haloethylsulfonyl and amino, an active methylene containing group and formyl, epoxy and carboxyl, aziridyl and amino, and aziridyl and carboxyl.

22. The analytical element of claim 1, further comprising at least one other zone permeable to the liquid.

23. The analytical element of claim 22, further comprising an interactive composition containing at least one component which undergoes an interaction with said analyte or a reaction or decomposition product thereof, said component being located in the other zone permeable to the liquid.

24. The analytical element of claim 22, wherein the other zone permeable to the liquid contains an immunoreagent.

25. The analytical element of claim 22, wherein at least one of the zones permeable to said liquid is a reagent zone which contains an interactive composition containing at least one component which undergoes an interaction with said analyte or reaction or decomposition product thereof to thereby release a colorimetric or fluorometric detectable species and wherein at least one other zone permeable to said liquid is a registration zone positioned between the support and the reagent zone and which receives the detectable species.

26. The analytical element of claim 22, wherein said other zone permeable to the liquid contains the bound particulate structure.

27. The analytical element of claim 26, wherein one of the zones having the bound particulate structure contains an immobilized antibody.

28. A method of detecting an analyte in an aqueous sample suspected of containing said analyte comprising:
(a) incorporating said sample and a labelled analyte in a first zone of the analytical element of claim 26 containing said bound particulate structure, said labelled analyte consisting essentially of the analyte to be detected or an analog thereof and a label capable of being detected by radiometric means;
(b) incorporating antibody for said labelled analyte in a second zone of said analytical element containing said bound particulate structure;
(c) permitting said analyte in said sample and said labelled analyte to undergo a competitive binding reaction with said antibody; and
(d) determining the amount of unbound labelled analyte present in said analytical element, said amount being proportional to the amount of analyte present in said sample.

29. A method of detecting an analyte in an aqueous sample suspected of containing said analyte comprising:
(a) incorporating said sample and a labelled analyte in a first zone of the analytical element of claim 26 containing said bound particulate structure, said labelled analyte consisting essentially of the analyte to be detected or an analog thereof and a label capable of being detected by radiometric means;
(b) incorporating antibody for said labelled analyte in a second zone of said analytical element containing said bound particulate structure;
(c) permitting said analyte in said sample and said labelled analyte to undergo a competitive binding reaction with said antibody; and
(d) determining the amount of bound labelled analyte present in said analytical element, said amount being inversely proportional to the amount of analyte present in said sample.

* * * * *